(12) United States Patent
Binder

(10) Patent No.: US 8,129,370 B2
(45) Date of Patent: Mar. 6, 2012

(54) USE OF OXICAM COMPOUNDS

(75) Inventor: Dieter Binder, Vienna (AT); Eva Binder, legal representative, Vienna (AT)

(73) Assignee: Dritte PatentPortfolio Beteiligungsgesellschaft MBH & Co. KG, Schonefeld/Waltersdorf (DE)

( * ) Notice: Subject to any disclaimer, the term of this patent is extended or adjusted under 35 U.S.C. 154(b) by 455 days.

(21) Appl. No.: 10/558,117

(22) PCT Filed: May 27, 2004

(86) PCT No.: PCT/AT2004/000185
§ 371 (c)(1),
(2), (4) Date: Mar. 2, 2007

(87) PCT Pub. No.: WO2004/105766
PCT Pub. Date: Dec. 9, 2004

(65) Prior Publication Data
US 2007/0275958 A1    Nov. 29, 2007

(30) Foreign Application Priority Data

May 27, 2003 (AT) .................................. A 819/2003

(51) Int. Cl.
*A61K 31/546* (2006.01)
(52) U.S. Cl. .................................................. 514/226.5
(58) Field of Classification Search ................ 514/226.5
See application file for complete search history.

(56) References Cited

U.S. PATENT DOCUMENTS

| 4,180,662 | A |   | 12/1979 | Pfister et al. ...................... 544/48 |
| 4,544,655 | A |   | 10/1985 | Pfister et al. ................ 514/222.8 |
| 5,643,960 | A | * | 7/1997 | Breitner et al. ................ 514/570 |
| 6,184,248 | B1 |   | 2/2001 | Lee et al. ...................... 514/474 |
| 6,187,756 | B1 |   | 2/2001 | Lee et al. ........................ 514/26 |
| 2002/0052407 | A1 |   | 5/2002 | Lee et al. ...................... 514/474 |
| 2002/0119193 | A1 |   | 8/2002 | Le et al. ........................ 424/465 |

FOREIGN PATENT DOCUMENTS

| JP | 54-48792 | 5/1979 |
| JP | 59-67292 | 4/1984 |
| JP | 1-149792 | 6/1989 |
| JP | 2001-525058 | 12/2001 |
| WO | WO 93/24115 | 12/1993 |
| WO | WO 01/78721 | 10/2001 |
| WO | WO 02/00167 | 1/2002 |

OTHER PUBLICATIONS

Golden. Dementia and Alzheimer's Disease. Clinical & Health Affairs, Minnesota Medicine, Jan. 1995, vol. 78, pp. 25-29.*
Laabich et al. Neuroprotective effect of AIP on N-methyl-D-aspartate-induced cell death in retinal neurons. Molecular Brain Research 85 (2000), 32-40.*
Veld et al. Nonsteroidal antiinflammatory drugs and the risk of Alzheimer's disease. The New England Journal of Medicine. vol. 345, No. 21, Nov. 22, 2001, pp. 1515-1521.*
Radhofer-Welte et al. Lornoxicam, a new potent NSAID with an improved tolerability profile. Drugs of Today 2000, 36(1): 55-76.*
Office Action issued in corresponding Japanese Application No. 2006-529424, dated Sep. 7, 2010 (English translation included).
Callingham, "Meeting Report: International conference on inflammo pharmacology and 5th side-effects of anti-inflammatory drugs symposium," *Inflammopharmacology*, 5:309-316, 1997.

* cited by examiner

*Primary Examiner* — Jennifer M Kim
(74) *Attorney, Agent, or Firm* — Fulbright & Jaworski LLP

(57) ABSTRACT

The invention relates to the use of lornoxicam or analogues thereof which inhibit cyclo-oxygenase 1 and cyclo-oxygenase 2 (COX 1 and COX 2), cannot penetrate the blood-brain barrier under physiological conditions, and reduce the prostaglandin E2-induced induction of the amyloid-precursor-protein (APP), for producing a pharmaceutical composition for the treatment or prevention of Alzheimer's disease or arteriosclerosis.

2 Claims, 7 Drawing Sheets

Fig. 4

| Compound | COX-1* Human HEL-Cells | COX-2* Human Macrophages | Ratio COX-1/COX-2 |
|---|---|---|---|
| LORNOXICAM | 0,003 | 0,008 | 0,38 |
| TENOXICAM | 0,32 | 0,13 | 2,44 |
| PIROXICAM | 0,45 | 0,77 | 0,58 |
| MELOXICAM | 1,46 | 0,10 | 14,21 |
| DICLOFENAC | 0,0006 | 0,017 | 0,04 |
| KETOROLAC | 0,025 | 0,039 | 0,64 |
| INDOMETACIN | 0,0045 | 0,045 | 0,10 |
| IBUPROFEN | 1,07 | 1,12 | 0,95 |
| ASPIRIN | 9,58 | 16,0 | 0,60 |

* $IC_{50}(\mu M)$

J. Berg et al. Inflamm. res. 48 (1999) 369-379

Lornoxicam pharmacokinetics in healthy young volunteers after oral single dose

| Dose (mg) | Number | Median $C_{max}$ [µg/L (SD)] | Median AUC 0–8 [µg·L⁻¹·h⁻¹ (SD)] |
|---|---|---|---|
| 2 | 6 | 133 (56) | 546 (342) |
| 4 [a] | 63 | 299 (63) – 363 (110) [a] | 1531 (567) – 1744 (348) [a] |
| 6 | 6 | 309 (92) | 1595 (592) |
| 8 [b] | 30 | 678 (151) – 822 (199) [b] | 2707 (680) – 3596 (1538) [b] |
| 16 | 18 | 1620 (439) | 8103 (3842) |

[a] Range of average values from 5 studies.
[b] Range of average values from 2 studies.
Abbreviations: AUC 0–8 = Range below time-plasma concentration curve; $C_{max}$ = peak-plasma-concentration.

Fig. 5

USE OF OXICAM COMPOUNDS

This application is a national phase application under 35 U.S.C. §371 of International Application No. PCT/AT2004/000185 filed 27 May 2004, which claims priority to Austrian Application No. A 819/2003 filed 27 May 2003. The entire text of each of the above-referenced disclosures is specifically incorporated herein by reference without disclaimer.

The invention relates to the production of pharmaceutical compositions for the treatment of Alzheimer's Disease and arteriosclerosis.

The etiology of Alzheimer's Disease (AD) has not yet been clarified. According to the "amyloid hypothesis" of AD, a change occurs in the cleavage of the amyloid precursor protein (APP). The so-called β-42 peptide is deposited, whereby cerebral plaques form. Also as a consequence of the resultant hypoperfusion, neuronal degeneration occurs.

The treatment methods currently employed all comprise the administration of cholinergic agents, in particular of inhibitors of acetylcholinesterase, since AD involves substantial losses of cholinergic neurons, and acetylcholinesterase inhibitors increase the acetylcholin level, so that the remaining neurons remain activated ("firing"). However, the progressive loss of neurons unfortunately cannot be stopped by this treatment.

Further target molecules, the influencing of which is currently being discussed and tested in the context of an AD therapy, are secretase-modulating substances, in particular β- and γ-secretase inhibitors, inhibitors of cholesterol biosynthesis, inhibitors of amyloid aggregation, immunological methods, in particular with the A-β peptide or antibodies against this peptide, prevention of the APP expression, increase of the APP clearance, modulation of the phosphorylation of tau protein and lowering of the serum amyloid P level (Wolfe, Nat. Rev. Drug Discov. 1 (2002) 859-866).

In US 2002/0052407 A1, U.S. Pat. No. 6,187,756 B1 and U.S. Pat. No. 6,184,248 B1, substance mixtures are disclosed which contain non-steroidal anti-inflammatory drugs (NSAID) for inhibiting an abnormal expression of the amyloid precursor protein (APP) which is known to be involved in Alzheimer's Disease. By means of in vitro and in vivo tests it could be shown in the examples that the inventive substances inhibit the over-expression of APP. All three documents suggest the use of non-steroidal anti-inflammatory drugs which only inhibit cyclooxygenase-2, yet not cyclooxygenase-1, for the prevention or possible healing of Alzheimer's Disease.

Furthermore, in these documents cyclooxygenase-2 inhibitors exclusively are claimed. Oxicams and, in particular, lornoxicam or analogous compounds are not disclosed therein.

In WO 93/24115 A1, a method for treating dementia, in particular Alzheimer's Disease, by administering non-steroidal anti-inflammatory drugs has been described. Besides a number of other substances, also oxicams, in particular piroxicam, isoxicam and sudoxicam have been suggested, yet not lornoxicam or analogous compounds.

In WO 01/78721 A1, a method for the prevention and/or for the healing of Alzheimer's Disease by administering substances that reduce the content of the amyloid-β-polypeptide (Aβ) A$β_{42}$ is described. Since a high expression rate of A$β_{42}$ is held responsible for the development of Alzheimer's Disease, the course of the disease can be positively influenced by reducing this polypeptide. In this document, moreover, a test is described in which the influence of various NSAIDs on the expression rates of two Aβ-polypeptides, A$β_{40}$ and A$β_{42}$, are shown. From this it results that oxicams, in particular meloxicam, peroxicam, isoxicam and tenoxicam (lornoxicam or analogous compounds thereof are not mentioned here) do not influence the expression of A$β_{42}$ and even increase the expression thereof, respectively. From this document, therefore, the person skilled in the art could derive that oxicams have proven as not advantageous to be used for the reduction of A$β_{42}$.

From US 2002/0119193 A1, pharmaceutical compositions are apparent which i.a. contain selective cyclooxygenase-2 inhibitors and are used for the treatment of various diseases, among them Alzheimer's Disease. According to this document, the inventive cyclooxygenase-2 inhibitors have advantages over the conventional, non-steroidal, anti-inflammatory active substances. Thus, also the teaching of this document leads away from the use of oxicams which inhibit both cyclooxygenase-1 and cyclooxygenase-2.

None of the previously described concepts, however, has actually enabled a breakthrough in the efficient treatment and, above all, in the prevention of AD. Therefore, medicinal treatment and prevention measures for AD are still urgently needed.

Accordingly, the present invention relates to the use of lornoxicam or lornoxicam analogues for producing a pharmaceutical composition for the treatment or prevention of Alzheimer's Disease (AD) or of arteriosclerosis.

Only recently it has been found that peripheral platelets are the primary source of the β-42 peptide deposited in the cerebral plaques. With this finding, AD is to be defined as a vascular disease. The new etiological interpretation is supported by the results of clinical studies which show that non-steroidal anti-inflammatory drugs (NSAIDs) alleviate symptoms of AD. These studies in turn were based on the hypothesis that AD were an inflammatory disease of the brain, various causes for the inflammatory symptoms having been mentioned. Thus, by administering from 100 to 150 mg of indometacin per day, the cognitive degradation could be reduced by approximately 9% over 6 months. Likewise, it has been known that NSAIDs have an influence on APP protein expression and processing in that they reduce the prostaglandin E2-induced APP expression and at the same time cause changes in the cleavage of APP.

In studies with Ibuprofen and Indometacin it could be demonstrated that the portion of the amyloid β-42 peptide is lowered and that of the non-amyloidogenic soluble APP is increased. From the fact that platelets are a primary source of the proteins in amyloid plaques, there also results a correlation to arteriosclerotic diseases.

Here, too, the NSAID-caused reduction of the APP expression in platelets, the change in the cleavage of the platelet-APP with a reduction of the plasma A-β and an increase in the non-amyloidogenic soluble APP, the reduction of the amyloid plaques in the cerebral vessels and the reduced cerebrovascular hypoperfusion are the basic mechanisms of the therapeutic effect.

Therefore, the present invention is based on the idea that the underlying cause of sporadic AD is a vascular disturbance and that the primary source of the cerebrovascular deposition of β-42 are the peripheral platelets.

With the use according to the invention, the expression of APP in platelets is selectively prevented, and the cleavage of platelet APP is influenced, wherein the plasma A-β level decreases and the level of non-amyloidogenic soluble APP increases. On account of the reduced plaque formation in the cerebral vessels, cerebro-vascular hypoperfusion does not occur, whereby the neurodegeneration is reduced.

One of the essential pre-requisites for the use according to the invention is that the inventive substance, i.e. lornoxicam or a lornoxicam-analogue, inhibits both central isozymes of the eicosanoid metabolism, i.e. COX-1 and COX-2. Particularly the fact that the isozyme COX-2 is associated with inflammatory processes has supported the prevailing opinion which suggested the use of COX-2-selective brain-effective drugs. However, since according to the above-mentioned new findings peripheral platelets expressing COX-1 only are the primary source of the plaque protein, according to the invention both inhibiting activities must be provided in an efficient treatment and prevention agent.

Since in the brain COX-2 is also constitutively expressed, with a view to the peripheral occurrence of the platelets, the brain-effectiveness of an active substance must be considered not only as undesirable, but, much rather, even as a disadvantage, since the inhibition of a constitutively expressed enzyme as a rule causes the inhibition of physiological processes and, thus, may cause drug side effects. Thus, also the property of the agents to be used according to the invention of not crossing the blood-brain barrier is an important characteristic according to the invention.

The effectiveness of lornoxicam or of lornoxicam analogues within the scope of the present invention has also been surprising in view of the prior art, in particular in view of the findings provided in WO 01/78721 A1, since the oxicams described there, in particular meloxicam, peroxicam, isoxicam and teroxicam, either could not influence the expression of $A\beta_{42}$ or even increased them.

According to the present invention, however, lornoxicam and its analogues have proved extremely advantageous in the treatment and, above all, in the prevention or slowing down of AD and arteriosclerosis. By "lornoxicam analogues" within the scope of the present invention all substances are to be understood which—derived from the lornoxicam structure—have the same basic effect in the peripheral platelets as lornoxicam or an effect comparable thereto with regard to Aβ-42, which means that they inhibit cyclooxygenase-1 and cyclooxygenase-2 (COX-1 and COX-2), cannot cross the blood/brain barrier under physiological conditions, and reduce the prostaglandin E2-induced induction of the amyloid precursor protein (APP).

Examples of such lornoxicam analogues are enolether of 6-chloro-4-hydroxy-2-methyl-N-(2-pyridyl)-2H-thieno(2,3-e)-1,2-thiazine-3-carboxylic acid amide-1,1-dioxide (as described in EP 0 313 935 A1, and in particular claimed by EP 0 313 935 B1), 4-hydroxy-2-methyl-3-(2-pyridylcarbamoyl)-6-trifluoromethyl-2H-thieno[2,3-e]-1,2thiozine-1,1-dioxide (as described in EP 0 103 142 A1 and in particular, claimed in EP 0 103 142 B1); thienothiazine derivatives according to EP 0 001 113 A1 (B1) having the general formula I

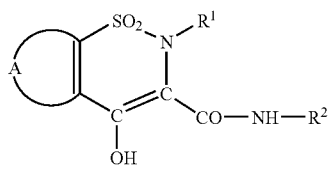

wherein A together with the two carbon atoms of the thiazine ring forms the group

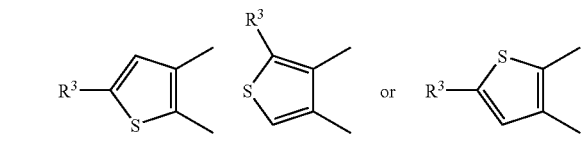

and the broken line indicates the double bond present in the first and in the last instance, $R^1$ represents lower alkyl, $R^2$ represents 2-thiazolyl, 4-methyl-2-thiazolyl, 4,5-dimethyl-2-thiazolyl, 5-methyl-1,3,4-thiadiazolyl, 2-pyrazinyl, 2-pyrimidinyl, 1,2,4-triazin-3-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6-dimethyl-2-pyridyl, 5-isoxazolyl, 5-methyl-3-isoxazolyl, 3,4-dimethyl-5-isoxazolyl, 2,6-dimethyl-4-pyrimidinyl, 1,2,3,4-tetrazol-5-yl or a phenyl residue optionally substituted by halogen, hydroxy, lower alkyl, trifluormethyl or lower alkoxy, and $R^3$ represents halogen, as well as salts thereof, wherein the term "lower alkyl" means straight-chain or branched saturated hydrocarbon groups with 1-4 carbon atoms, such as, e.g., methyl, ethyl, propyl, isopropyl and t-butyl; the term "lower alkoxy" relates to hydrocarbonoxy groups with up to 4 C atoms, and the term "halogen" refers to the 4 halogens chlorine, bromine, fluorine, iodine; particularly preferably, $R^3$ represents chlorine or bromine, wherein chlorine is particularly preferred; $R^1$ preferably represents the methyl group; $R^2$ preferably represents 2-thiazolyl, 5-isoxazolyl or 2-pyridyl; A preferably is the group

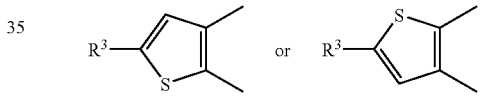

further preferred are [3aα, 8bα)]-1,2,3,3a,4,8b-hexahydropyrrolo[3',2':4,5]-cyclopenta[1,2-c]pyridine derivatives of the general formula

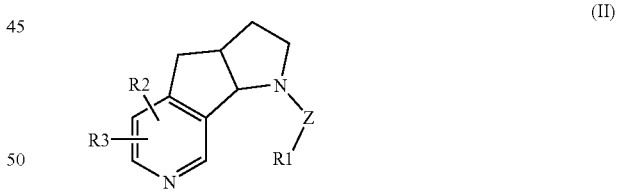

(II)

or [3aα, 8bα)]-1,2,3,3a,4,8b-hexahydropyrrolo[2',3':3,4]-cyclopenta[1,2-b]pyridine-derivatives of the general formula (III)

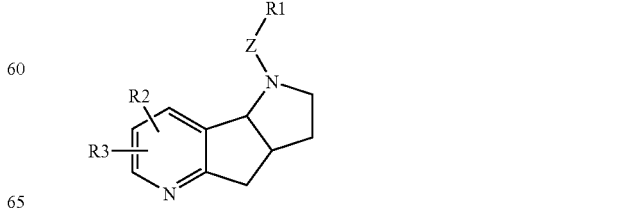

wherein:

Z represents a single bond or $CH_2$,

R1 represents hydrogen or a straight-chain or branched, optionally unsaturated lower-alkyl residue which may also be perfluorinated, R2 and R3 independently represent hydrogen, a straight-chain or branched, optionally unsaturated lower alkyl residue which may also be perfluorinated, lower-alkoxy, lower-alkyl-thio or halogen, as well as their optically pure antipodes and pharmaceutically usable salts.

Compounds of the general formulas (II) and (III) can be produced by reductively converting a compound

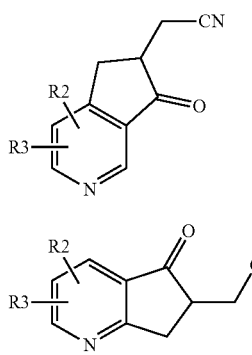

(IVa)

(IVb)

wherein R2 and R3 are as defined above, into the compound of the general formula II or III, wherein Z=single bond and R1=hydrogen, optionally reacting it with enantiomerically pure 1-phenylethyl-isocyanate to the compound of the general formula

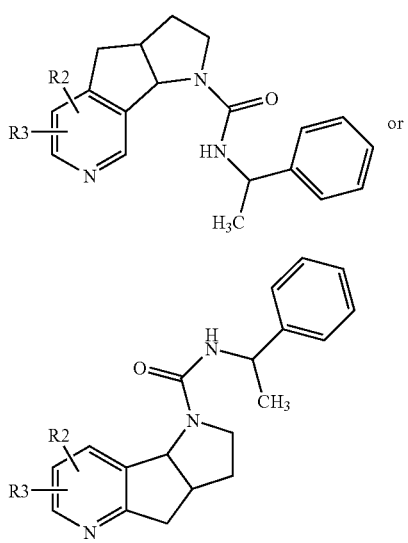

(Va)

or (Vb)

recovering from the thus obtained diastereomeric mixture the less readily soluble diastereomer by crystallization, cleaving the thus obtained diastereomerically pure compound of the general formula (Va) or (Vb) under suitable conditions to the enantiomerically pure compound of the general formula (II) or (III), wherein Z=single bond and R1=hydrogen, optionally reacting it under alkylating conditions to compounds of the general formula (II) or (III), wherein Z=$CH_2$, and optionally converting the compound of the general formula (II) or (III) as well as its racemic mixture into its pharmaceutically usable salts, wherein the term "lower alkyl" means a straight-chain or branched alkyl residue with 1-4 carbon atoms, e.g. methyl, ethyl, n- and i-propyl, n-, i- and t-butyl; the term "lower alkoxy" means a straight-chain or branched alkoxy residue with 1-4 carbon atoms, e.g. methoxy, ethoxy, n- and i-propoxy, n-, i- and t-butoxy; the term "lower-alkyl-thio" means a straight-chain or branched alkyl-thio residue with 1-4 carbon atoms, e.g. methyl-thio, ethyl-thio, n- and i-propyl-thio, n-, i- and t-butyl-thio; and the term "halogen" means fluorine, chlorine, bromine or iodine.

The reactions according to the invention are best carried out by dissolving the compound of the general formula (IVa) or (IVb) in a polar solvent, such as, e.g., acetic acid ethyl ester, dioxane, ethanol or methanol, admixing 1-5 equivalents of a suitable catalyst, such as, e.g., W2-Raney Nickel or Raney Cobalt and the like, and hydrogenating at 40 to 70° C. up to a stoichiometric hydrogen uptake. For separation of the enantiomers, the thus obtained racemic compound of the general formula (II) or (III), wherein Z=single bond and R1=hydrogen, can be reacted in an inert solvent, such as, e.g., tetrahydrofurane, dioxane or acetone, with 1 equivalent (+) or (−) 1-phenylethylisocyanate to obtain a compound of the general formula (Va) or (Vb), and from the diastereomeric mixture thus obtained, the less readily soluble diastereomer can be recovered by crystallization. For cleavage the thus obtained diastereomerically pure compound of the general formula (Va) or (Vb) is dissolved in a high-boiling alcohol, such as, e.g., propanol, butanol, pentanol, glycol etc. or the aqueous mixtures thereof, and heated for 1-24 hours to boiling with 5-20 equivalents of a base, such as sodium propanolate, -butanolate, -pentanolate or sodium hydroxide. The thus obtained enantiomerically pure compound of the general formula (II) or (III), wherein Z=single bond and R1=hydrogen, as well as its racemic form, optionally is dissolved for alkylation in an inert solvent, such as, e.g., tetrahydrofurane, dioxane, acetonitrile or dimethylformamide etc., admixed with 1-20 equivalents of the compound of the formula

R1-CHO (VI), wherein R1 is as defined above, and 1.5-4 equivalents of a reducing agent, such as, e.g., sodium cyanoboro-hydride or the like, and reacted at −20° C. to 100° C. for between 1 and 24 hours.

The compounds of the general formula (II) or (III) obtained in this reaction are basic compounds and can be converted into their pharmaceutically compatible salts in a conventional manner by means of inorganic or organic acids. Salt formation can be effected e.g. by dissolving the compounds of the formula (II) or (III) in a suitable solvent, e.g. water, a lower aliphatic alcohol, THF, dioxane, benzene, diethyl ether, DMF or DMSO, admixing an equivalent amount of the desired acid, providing for a good mixing and withdrawing the solvent under vacuum when the salt formation has been completed. Optionally, the salt can be re-crystallized after isolation.

Further preferred examples of the inventive lornoxicam analogues are the subject matter of AT 400 567 B and of AT 400 437 B, in particular the substances described in claims 2, 3, 4, 5, 6, 7, 8, 9, 10, 11 or 12 of AT 400 567 B and in claims 2, 3 or 4 of AT 400 437 B. Further lornoxicam analogues preferred according to the present invention are disclosed in EP 0 657 459 A1, in particular the substances claimed in claims 2, 3 and 4 thereof.

Pharmaceutically usable salts are those of strong inorganic acids, such as, e.g., hydrochloric acid, hydrobromic acid, sulfuric acid etc., but also those of organic acids, such as, e.g., fumaric acid, citric acid, sebacic acid, etc.

Preferably, the administration of the substance should not entail any severe undesired events, i.e. it should be free from side-effects. By this, the prophylactic intake of this substance for preventing AD or arteriosclerosis becomes possible without confronting the patient with undesired side reactions. A prophylactic treatment is primarily indicated for those persons who have a high risk of AD or arteriosclerosis, be it by genetically caused circumstances (familial accumulation of such diseases) or by other parameters. For defining the freedom from side-effects according to the present invention, the definitions provided in relevant pharmaceutical textbooks and standard literature can be resorted to. For example, the side-effects found during observation of usage should be below 1%, preferably below 0.5%, more preferably below 0.1%, in particular below 0.05%. Optionally, the substances according to the invention can be combined with further drugs, particularly those which counteract possible negative effects, such as, e.g., gastric mucosa initiating properties, (e.g. antacids, H2 receptor antagonists, proton pump inhibitors, . . . ). This must be considered primarily in case of long-term applications.

Besides lornoxicam, substances particularly preferred to be used within the scope of the present invention are primarily
6-chloro-4-(1-(ethoxycarbamoyloxy)-ethoxy)-2-methyl-N-(2-pyridyl)-2H-thieno-(2,3-e)-1,2-thiazine-3-carboxylic acid amide-1,1-dioxide,
6-chloro-4-hydroxy-2-methyl-3-(2-pyridyl-carbamoyl)-2H-thieno[3,2-e]1,2-thiazine-1,1-dioxide,
(+)-[3aα,8bα)]-1,2,3,3a,4,8b-hexahydropyrrolo[2',3':3,4] cyclopenta[1,2-b]pyridine-dihydrochloride;
(+)-[3aS-(3aα,8bα)]-1,2,3,3a,4,8b-hexahydropyrrolo-[3',2':4,5]cyclopenta[1,2-c]pyridine-dihydrochloride;
(−)-[3aR-(3aα,8bα)]-1,2,3,3a,4,8b-hexahydropyrrolo-[3',2':4,5]-cyclopenta[1,2-c]pyridine-dihydrochloride;
(−)-[3aα,8bα)]-1,2,3,3a,4,8b-hexahydropyrrolo-[2',3':3,4]-cyclopenta[1,2-b]pyridine-dihydrochloride;
(−)-[(3aα,8bα)]-1,2,3,3a,4,8b-hexahydro-1-methyl-pyrrolo-[2',3':3,4]-cyclopenta[1,2-b]pyridine-dihydrochloride;
(+)-[3aS-(3aα,8bα)]-1,2,3,3a,4,8b-hexahydro-1-methyl-pyrrolo-[3',2':4,5]-cyclopenta[1,2-c]pyridine-dihydrochloride;
(+)-[3aα,8bα]-1,2,3,3a,4,8b-hexahydro-1-methyl-pyrrolo-[2',3':3,4]-cyclopenta[1,2-b]pyridine-dihydrochloride;
(+)-[3aS-(3aα,8bα)]-1,2,3,3a,4,8b-hexahydro-1-methyl-pyrrolo-[3',2':4,5]cyclopenta[1,2-c]pyridine-dihydrochloride.

The particular advantage according to the invention of the application of lornoxicam as well as of the lornoxicam analogues results from a particularly advantageous combination of the pharmacodynamic and pharmacokinetic properties of this active substance.

According to the present invention, the pharmacodynamic particularities of lornoxicam or lornoxicam analogues causing the invention are the following:

One particularly important property which causes the particular inventive suitability of lornoxicam resides in the fact that the substance inhibits both central isozymes of the eicosanoid metabolism, i.e. COX-1 and COX-2. The henceforth established fact that peripheral platelets expressing COX-1 only, are the primary source of the plaque protein, is the reason for the superiority of the inventive application of lornoxicam and its analogues, respectively, which have a significant inhibition of COX-1.

Moreover, lornoxicam is an active substance with a particularly high intrinsic activity. Since a therapy for the prevention of AD and of arteriosclerosis, respectively, must last over an extended period of time, a reduced load of active substance on the body constitutes a further advantage.

Furthermore, lornoxicam is not capable of crossing the blood-brain barrier (Pruss et al., 3. Interscience World Conference on Inflammation, Monte Carlo (1989), Abstract 41).

In view of the extended duration of a preventive therapy of AD with lornoxicam, the short plasma half-life of lornoxicam is a special advantage since by this a cumulation in blood will not occur. Likewise, the known good gastro-intestinal and other tolerance of the active substance is of great importance. Thus, in one million of prescriptions, less than 10 severe undesired events have been reported, and the side-effects found during observation of usage have been far below 0.05% (wherein so far all the side effects could be repaired again).

The said combination of pharmaco-dynamic and pharmaco-kinetic properties of the active substance lornoxicam in a constellation which is particularly favorable for the purpose of the therapy of AD and of arteriosclerotic diseases is not found in any other hitherto known substance in a comparable way.

The invention will be explained in more detail by way of the following examples as well as the drawing figures to which, however, it shall not be restricted.

Therein,

FIG. 4 shows the COX-inhibiting effect of some substances;

FIG. 5 shows the lornoxicam pharmaco-kinetics in healthy young volunteers after an oral single dose;

EXAMPLES

Example 1

Figure 1:
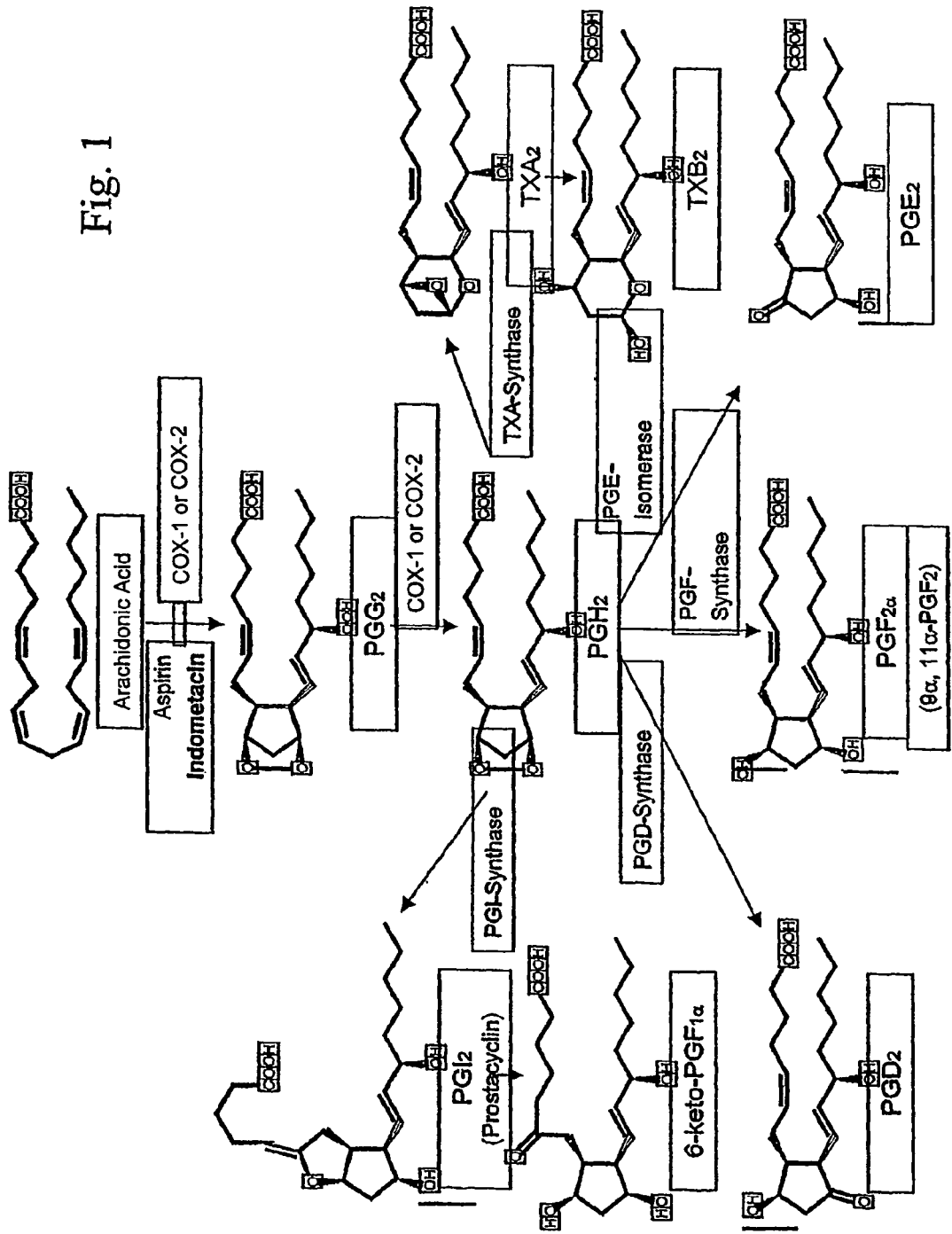
FIGS. 1, 2 and 3 show the arachidonic acid pathway and its correlation with COX-1 and COX-2.
Figure 2:
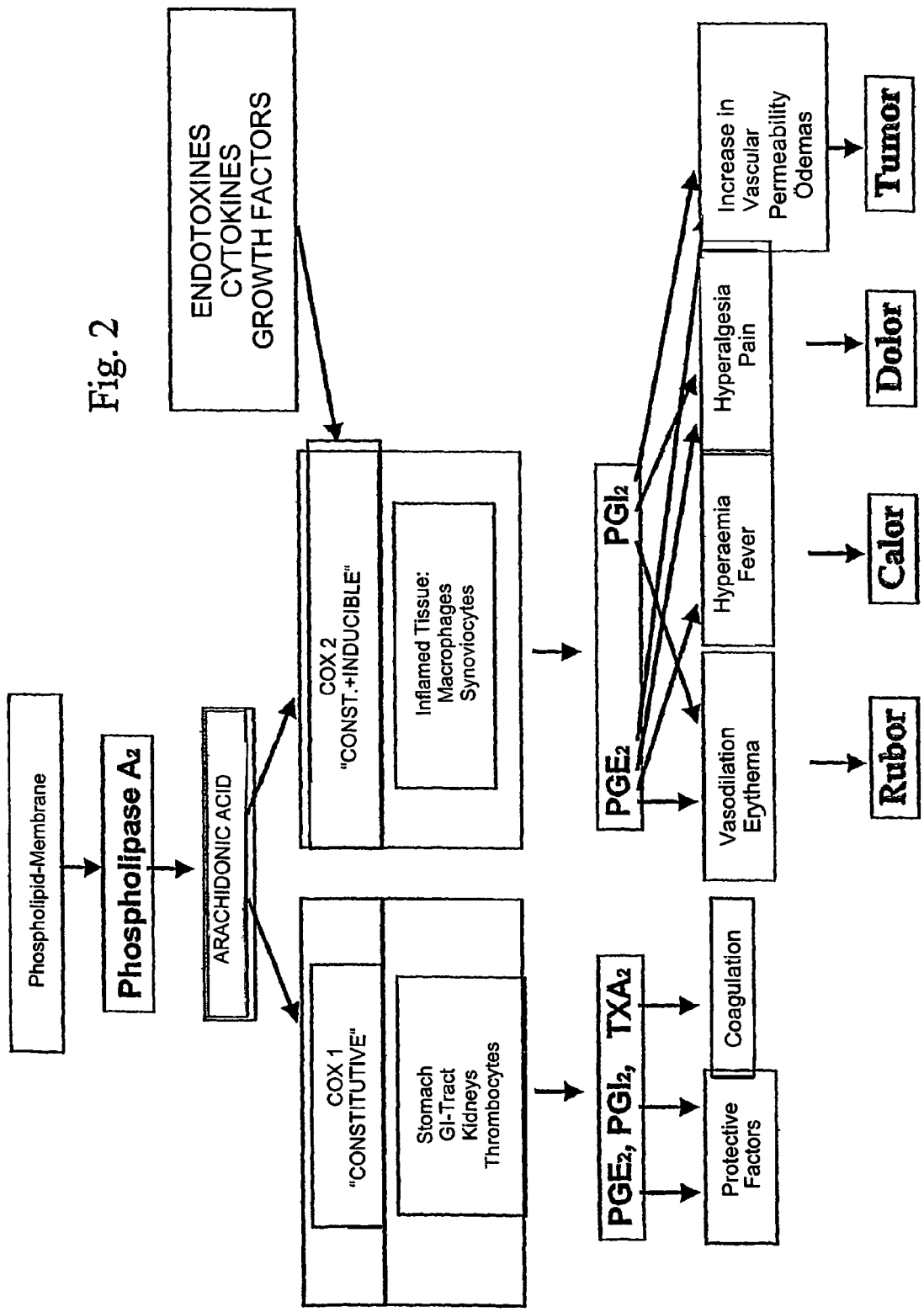
Figure 3:
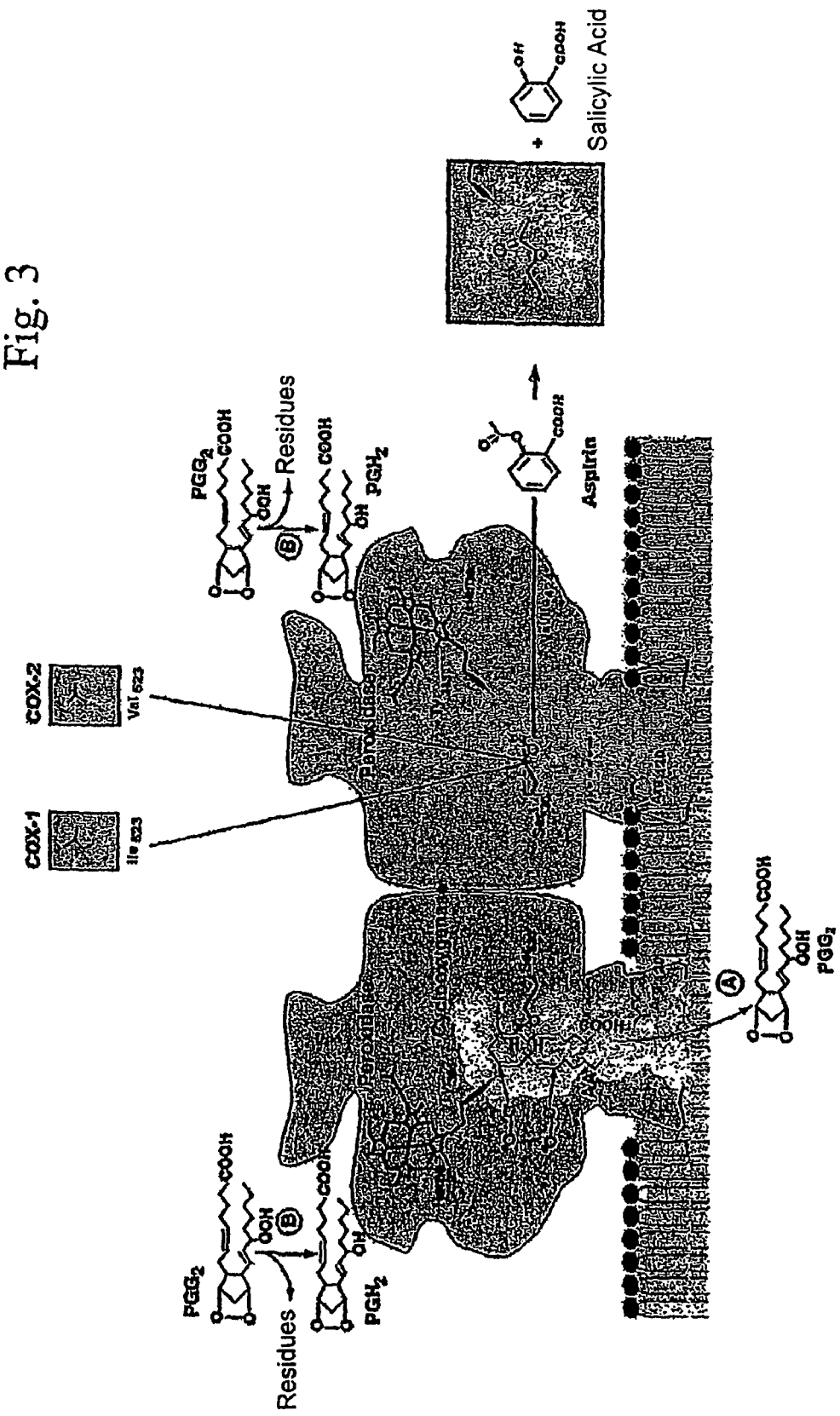
Figure 6:
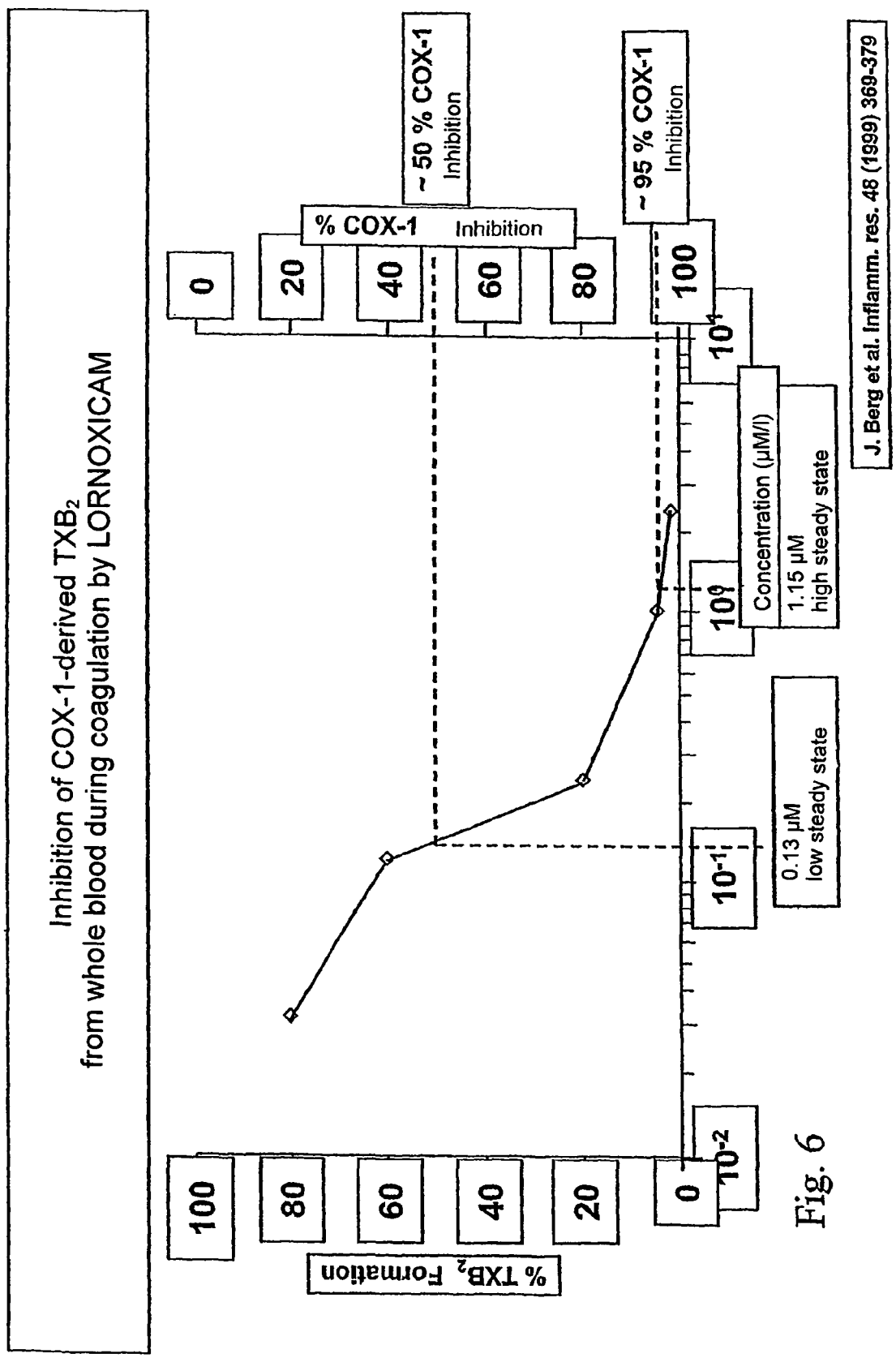
FIG. 6 shows the inhibition of COX-1-derived TXB2 from whole blood during coagulation by lornoxicam.
Figure 7:
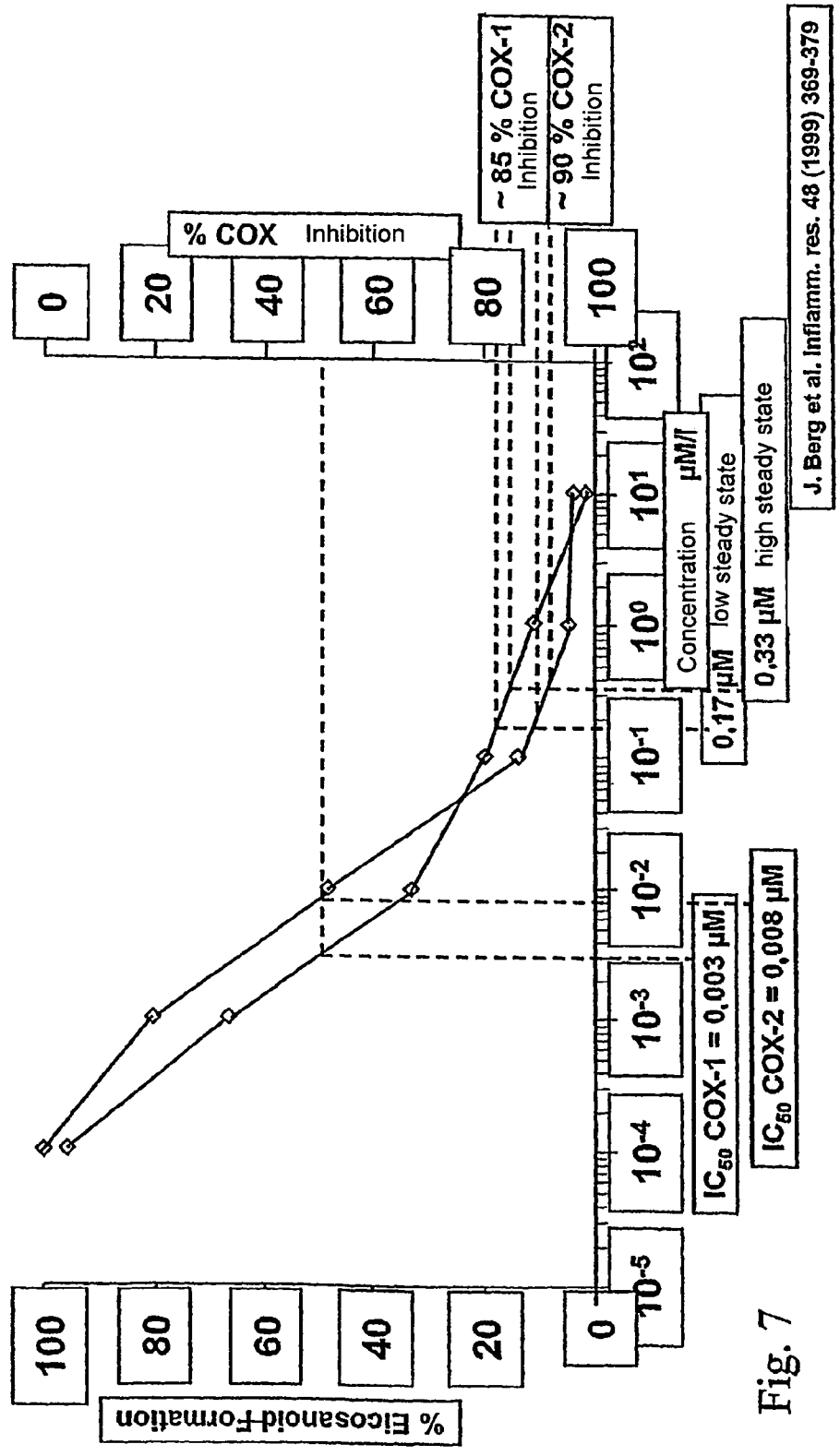
FIG. 7 shows the inhibition of the eicosanoid formation in HEL cells (COX-1) and LPS-stimulated Mono Mac 6-cells (COX-2) by lornoxicam.

Effect of Lornoxicam on APP Processing In Vitro and In Vivo 1.1. Characterization of a Specific Influence on APP Cleavage in Vitro:
1.1.1. Influence of Lornoxicam on APP Processing in Neuronal Cell Line (SH-SY5Y)
Release of the amyloid β-42 peptide (lowered by NSAIDs)
Release of the non-amyloid sAPPα protein (increased by NSAIDs)
Expression of the APP holoprotein (lowered by NSAIDs)
1.2. Characterization of Human Thrombocytes as Peripheral Model for the Effect of Lornoxicam on Nerve Cells In peripheral thrombocytes of patients suffering from Alzheimer's Disease it has been demonstrated that the non-amyloid sAPPα protein is also produced in a reduced amount (Colciaghi et al., Mol. Med. 8 (2002), 67-74). The expression of the non-amyloid sAPPα can be increased in nerve cells by NSAIDs (Avramovich et al., J. Biol. Chem. 277 (2002), 31466-73). The results of these two studies lead to the expectation that the non-amyloid sAPPα protein is very well suited to peripherally observe the specific activity of lornoxicam.
1.2.1. Influence of Lornoxicam on APP-Processing in Human Thrombocytes In Vitro Release of non-amyloid sAPPα protein of activated thrombocytes 1.2.2. Influence of Lornoxicam on APP-Expression of Human Thrombocytes of Alzheimer's Disease Patients In Vivo Expression of APP-holoprotein (This parameter is meaningful if lornoxicam does not have a specific influence on APP processing, since APP holoprotein is expressed in increased amounts in the frontal cortex (Golde et al., Neuron 4 (1990), 253-267) and NSAIDs can reduce its expression. In an ongoing study, also increased APP holoprotein expression has been demonstrated on thrombocytes of Alzheimer patients).

APP ratio of the thrombocytes of Alzheimer's Disease patients before and after treatment with lornoxicam.

Release of the non-amyloid sAPPα protein of activated thrombocytes

These investigations are aimed at the in vivo-monitoring on peripheral blood thrombocytes for the postulated effect of lornoxicam on nerve cells.

2.2. Protein-Profiling (Proteomics) of Human Thrombocytes After In Vivo Administration of Lornoxicam Comparison of the thrombocyte proteome of Alzheimer's Disease and healthy individuals before and after lornoxicam medication.

These investigations were aimed at the in vivo-protein profiling of the effect of lornoxicam on human thrombocytes.

2.3. Influence of Lornoxicam on the Pharmacoproteomics of Human Thrombocytes In Vitro: Protein-Profiling (Proteomics) of Human Thrombocytes After In Vitro Incubation with Lornoxicam Comparison of the thrombocyte proteome of lornoxicam-treated thrombocytes with non-treated control thrombocytes.

This example is aimed at the characterization of the thrombocyte proteins which are directly affected by the cyclooxygenase-inhibitor lornoxicam.

The invention claimed is:

1. A method of treating Alzheimer's Disease (AD) in a subject comprising administering a lornoxicam analogue selected from the group consisting of 6-chloro-4-(1-(ethoxy-carbamoyloxy)-ethoxy)-2-methyl-N-(2-pyridyl)-2H-thieno-(2,3-e)-1,2-thiazine-3-carboxylic acid amide-1,1-dioxide and 6-chloro-4-hydroxy-2-methyl-3-(2-pyridyl-carbamoyl)-2H-thieno[3,2-e]1,2-thiazine-1,1-dioxide to the subject in need thereof, wherein neurodegeneration associated with Alzheimer's Disease is reduced in the subject.

2. The method of claim 1, wherein the subject is a human.

* * * * *